United States Patent [19]
Groves

[11] Patent Number: 4,525,666
[45] Date of Patent: Jun. 25, 1985

[54] CELL BREAKDOWN

[75] Inventor: Michael R. Groves, Flemington, N.J.

[73] Assignee: Coulter Electronics, Inc., Hialeah, Fla.

[21] Appl. No.: 374,222

[22] Filed: May 3, 1982

[51] Int. Cl.³ ............................................. G01N 27/07
[52] U.S. Cl. .................................. 324/71.1; 324/71.4
[58] Field of Search ................. 324/71 CP, 71.1, 71.4, 324/71 R, 65 R, 58.5 R; 377/10, 11, 12

[56] References Cited

U.S. PATENT DOCUMENTS

| | | | |
|---|---|---|---|
| 3,502,974 | 5/1966 | Coulter et al. | 324/71.1 |
| 3,549,994 | 12/1970 | Rothermal et al. | 324/71.1 |
| 3,793,587 | 2/1974 | Thom et al. | 324/71.1 |
| 3,821,644 | 6/1974 | Gohde et al. | 324/71.1 |
| 4,220,916 | 9/1980 | Zimmermann et al. | 324/71.1 |

*Primary Examiner*—Ernest F. Karlsen
*Attorney, Agent, or Firm*—Gerald R. Hibnick

[57] ABSTRACT

A particle analyzing apparatus for studying a stream of membrane-sheathed particles in liquid suspension wherein, for a given particle, a first particle pulse signal is obtained from a first sensing aperture having a first low frequency electrical field with an intensity below that causing particle electrical breakdown; a second particle pulse signal is obtained from a second sensing aperture having a second low frequency electrical field with an intensity equal to or greater than that causing particle electrical breakdown; a third particle pulse signal is obtained from one of the sensing apertures by having a high frequency electrical field therein or, alternatively, from a third sensing aperture having a third low frequency electrical field with a second and different intensity equal to or greater than that causing particle electrical breakdown. The three signals are correlated on a cell by cell basis and are used to determine the particles' apparent breakdown field intensity size and opacity, which in turn can yield particle volume, shape and internal conductivity.

7 Claims, 5 Drawing Figures

CELL BREAKDOWN

FIELD OF THE INVENTION

The invention pertains to a method for obtaining the electrical resistance measurements, including the breakdown field, for biological cells immersed in an electrolyte, to thereby extract the cellular volume, shape and internal conductivity.

BACKGROUND OF THE INVENTION

Cell and particle counting and measuring instruments, examples being those sold under the trademark Coulter Counter ® by Coulter Electronics, Inc., Hialeah, Fla., employ electronic sensing means which directly respond to the electrical resistance of each cell to count and measure each cell and progressively record cell parameters of a sample of cells suspended in an isotonic electrolyte solution. The Coulter Counter ® particle measuring instruments operate upon the well-known and documented principle of particle and cell measurement employing a sensing aperture path, which also is disclosed in Coulter U.S. Pat. No. 2,656,508 and improvement U.S. Pat. No. 3,259,842.

In the commercial Coulter Counter ® particle analyzer constructed in accordance with the heretofore mentioned U.S. Pat. No. 2,656,508, field excitation has been supplied by a direct current or low frequency source. As previously described, the electrical change caused by the passage of a particle through the electric field of small dimensions, excited by a direct or low frequency current, is approximately proportional to particle size. A direct current is considered to be of zero frequency in this application. However, the impedance sensing principle has been materially expanded to provide information concerning particles being studied, not limited only to characteristics due to the size of particles, but including characteristics due to the composition and nature of the material constituting the particles, as disclosed in U.S. Pat. No. 3,502,974 to Coulter et al. and U.S. Pat. No. 3,502,973 to Coulter et al. These prior art apparatuses generally have at least two current sources, both of which are applied to the sensing zone simultaneously, one having a radio frequency and the other being a "zero frequency" direct current or, alternatively, having a sufficiently low frequency that the reactive part of the particle impedance has a negligible effect on the response of the apparatus. At radio frequencies, the membrane capacitance shunts the cell's membrane resistance so that the high frequency measurement gives a size measurement which is a function of the cell's size and its internal conductance. One of the useful particle descriptors that can be obtained from this dual source arrangement is known in the art as the "opacity" of the particles. With a biological cell, opacity approximately measures the internal conductivity of the cell. Opacity also can be described as measuring the ratio of size as measured at radio frequency to size as measured at low or zero frequency.

U.S. Pat. No. 3,831,087 to Schulz et al., owned by the Assignee of the present invention, shows that as the electrical field strength increases in an electronic particle sensing aperture of the above-described type, electrical breakdown of the cells' membranes will occur at critical field strengths, resulting in the cells having a lower electrical resistance. The breakdown characteristics of cells, processed on a bulk basis, are shown by a graph of apparent mean cell volume (MCV) versus electrical aperture current. The data from processing a blood sample normally defines a breakdown curve having a first leg, the slope of which is representative of the average size and shape of the cells, and a second leg, the slope of which is representative of the average size, shape and internal conductivity of the cells, as shown and described in the Schulz patent. By ratioing the slope of the second leg with that of the first leg, the resulting ratio basically measures the average internal conductivity of the cells. The point of intersection of the two legs is described as the average breakdown point of the cells. The drawback of this technique is that only average values for a batch of cells can be obtained and, with the structure and techniques of the Schulz patent, the cells cannot be individually examined on a cell by cell basis. The average effect eliminates meaningful data on cell characteristics.

U.S. Pat. No. 3,560,847 to Boyd discloses a particle analyzer arrangement wherein the particle suspension through the sensing aperture is stopped momentarily, so that a single particle is in the sensing aperture. With the particle in the aperture, a ramp voltage is applied, allowing the breakdown curve to be generated for a single cell. Although this technique appears to provide breakdown information on a cell by cell basis, it is not practical to use this technique, due to heating of the liquid by the electrical current when stopped in the sensing aperture and further due to the extra difficulty in stopping the fluid stream in the sensing aperture to allow a single particle to be positioned therein. More specifically, although the heating problems are lessened by the short sensing aperture of FIG. 2 of Boyd, the particle alignment problems of having the particle coincident with the sensing aperture are increased. On the other hand, in FIG. 3 of Boyd, the elongated sensing aperture decreases the particle alignment problem, but increases the heating problem.

In an article entitled "Application of the Electrical Sizing Principle of Coulter to a New Multiparameter System", *IEEE Transactions of Biomedical Engineering*, Volume BME-27, No. 7, July 1980, pp. 364–369, by the Applicant herein, the volume, breakdown voltage and internal conductivity is determined for each cell, thereby overcoming the previously described problems associated with bulk processing and averaging effects therefrom. In this particle analyzer arrangement, a voltage ramp is applied across the orifice as a particle approaches. As the particle passes through the orifice, the field strength increases and breakdown is observed by a change in slope of the ramp signal, the degree of this change yielding the underestimation of the cell volume after breakdown. In order to accommodate the dynamic range of the particle pulse signals, a differential aperture-amplifying system is used and includes a pair of sensing apertures that are fluidly and electrically in parallel, one being used as a reference (no particles pass therethrough) and the other being used for measuring the particles. This same structure and technique is described in U.S. Pat. No. 4,220,916 to Zimmerman et al. This arrangement has the drawback of requiring relatively long orifices or low flow rates to allow enough time for applying the voltage ramp while the particle remains within the sensing aperture. Also, avoiding particle coincidence problems in long orifices mandates very dilute particle suspensions. Additionally, the dynamic impedance of the apertures as a function of applied current or field, as described in the above-mentioned IEEE article, complicates both the measurement and the electronics.

In the above-mentioned article, the phenomenon of the dielectric breakdown of a cell membrane and the consequences of the same are described. Briefly described, dielectric breakdown of a cell membrane is a phenomenon characterized by a reversible increase in the membrane conductance in response to an externally applied electric field pulse across the cell membrane. Once a critical membrane potential, i.e., breakdown voltage, has been reached, the membrane breaks through and becomes permeable to ions. The breakdown probably reflects the elastic and dielectric properties of the membrane. The critical breakdown field is altered in the presence of membrane agents and possibly by diseases. Breakdown in an electronic particle analyzer is detected by the underestimation of size after breakdown has occurred. Due to the increase in membrane conductance, the current lines pass partly through the cell interior, which is more conductive than the original membrane, leading to a reduction in the particle induced signal. The degree of underestimation depends on the internal conductivity and field induced increase in membrane conductance of the cell in relation to the external conductivity.

U.S. Pat. No. 3,793,587 to Thom et al. is of interest for showing back to back particle sensing apertures.

U.S. Pat. Nos. 3,502,973 to Coulter et al. and 3,502,974 to Coulter et al. are incorporated by specific reference herein.

SUMMARY OF THE INVENTION

The present invention is directed toward a particle analyzing apparatus for studying a stream of membrane-sheathed particles in liquid suspension, wherein the particles each undergo electrical breakdown in an electrical field having at least a minimum electrical breakdown field intensity. The particle sensing apparatus comprises at least two sensing aperture means, a first sensing aperture means and a second sensing aperture means; means for moving the liquid suspension of the particles through both of the sensing aperture means; first field generating means, for providing a low frequency first electrical field in the first sensing aperture means, having an electrical field intensity which is smaller in magnitude than the minimum electrical breakdown field intensities; first detecting means responsive to electrical impedance variations, for generating a first particle pulse signal with the passage of a particle through the first sensing aperture means; second field generating means, for providing a low frequency second electrical field in the second sensing aperture means, having an electrical field intensity which is at least as great in magnitude as the minimum electrical breakdown field intensities; second detecting means responsive to electrical impedance variations for generating a second particle pulse signal with the passage of the particle through the second sensing aperture means; and means for correlating the first particle pulse signal and the second particle pulse signal for the particle.

The above-described two particle pulse signals are generated by low frequency electrical fields which, for the purpose of describing this invention, are defined to include D.C. fields. The providing of these two particle pulse signals is useful by itself for detecting individual cells in different pathological states, e.g., with differing internal conductivities or deformabilities.

A third particle pulse signal is obtained in a sensing aperture by a high frequency current or, alternatively with a second, but different, low frequency field intensity in the range of intensities that cause electrical cell breakdown. With the addition of the third particle pulse signal, an apparent particle breakdown parameter, in the form of an electrical particle breakdown field intensity or voltage, is determined on a particle by particle basis. In one embodiment, this third particle pulse signal is obtained by generating a high frequency current in one of the first or second sensing apertures. In an alternative embodiment, the third particle pulse signal is obtained by adding a third sensing aperture having a low frequency field therein.

Since it is known that the actual breakdown potential across a biological cell's membrane remains fairly constant from cell to cell, the determination of the above-described breakdown parameter allows for the calculation of shape and deformability information on a cell by cell basis.

BRIEF DESCRIPTION OF THE DRAWINGS

Further objects and advantages of the present invention will become apparent as the following description proceeds, taken in conjunction with the accompanying drawing in which.

DETAILED DESCRIPTION OF THE PREFERRED EMBODIMENT

Figure 1:
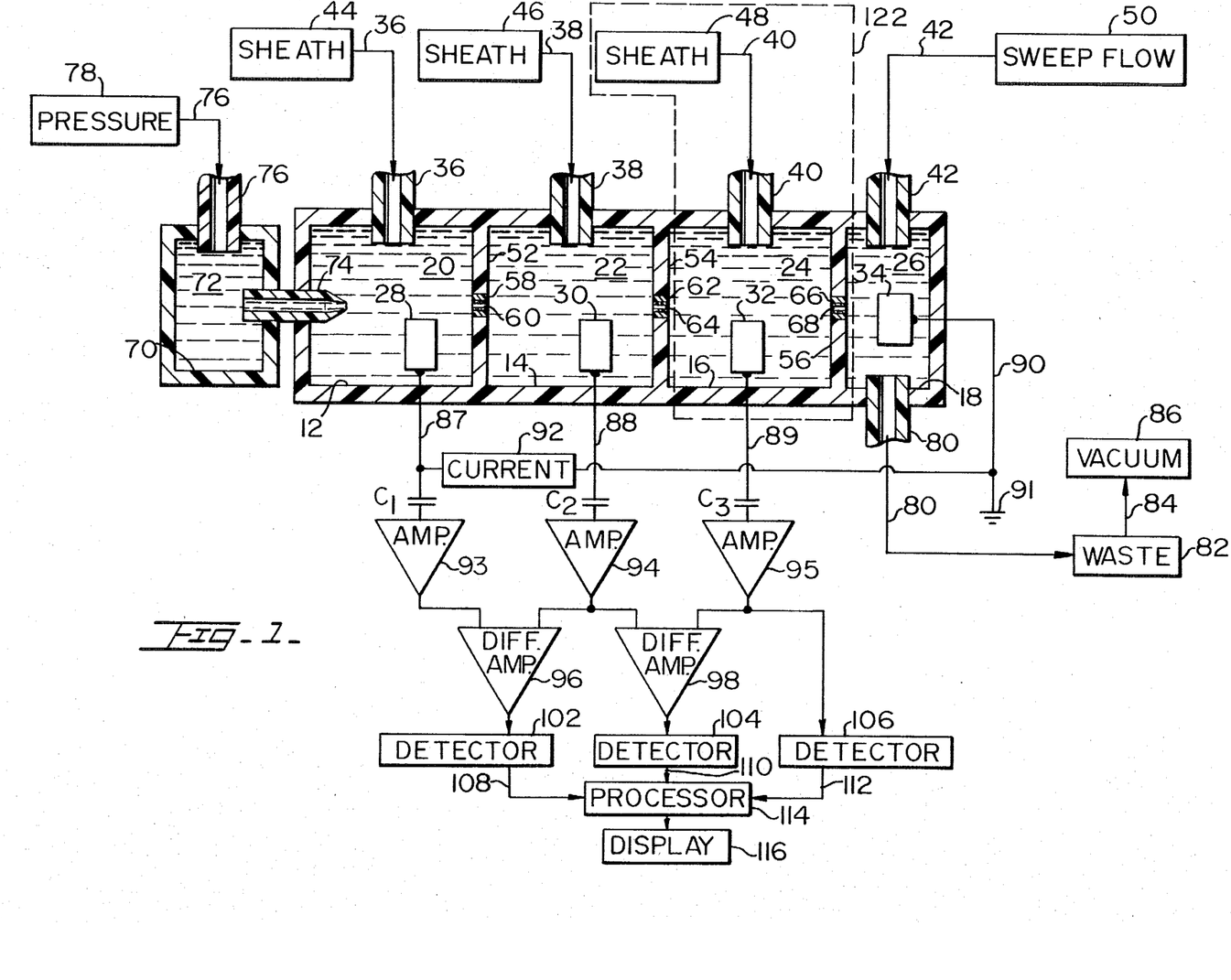
FIG. 1 is a diagrammatical view of the preferred embodiment of the particle analyzing apparatus according to the invention.

In FIG. 1, there is shown a preferred embodiment of a particle analyzing apparatus 10 having a plurality of chambers 12, 14, 16 and 18, respectively, for containing, respectively, bodies of saline solutions 20, 22, 24 and 26 and, respectively, a plurality of electrodes 28, 30, 32 and 34 and which are coupled, respectively, to a plurality of fluid conduits 36, 38, 40 and 42. Liquid for sheaths are provided to the chambers 12, 14 and 16 from a plurality of pressurized liquid reservoirs 44, 46 and 48, respectively, by way of the conduits 36, 38 and 40, respectively. Liquid for a sweep flow is provided from a liquid reservoir 50 to the chamber 18 by way of the conduit 42. A plurality of dividing walls 52, 54 and 56 separate adjacent chambers and have mounted therein, respectively, a wafer 58 having a first sensing aperture 60 formed therein, a wafer 62 having a second sensing aperture 64 formed therein, and a wafer 66 having a third sensing aperture 68 formed therein. A sample container 70 for containing the particle sample suspension 72, such as blood cells, is fluidly connected, in a conventional manner, to the chamber 12 by way of a focusing tube 74. The sample container 70 is fluidly connected by way of a fluid conduit 76 to a pressure source 78. The chamber 18 is fluidly connected by way of a fluid conduit 80 to a waste reservoir 82, which in turn is in fluid communication, by way of a conduit 84, with a vacuum source 86. In a well known manner, the relative pressures of the various containers and reservoirs are adjusted so that there is a pressure drop across each of the sensing apertures 60, 64 and 68. For example, a vacuum can be applied by the vacuum source 86 and the pressure source 78 can consist of opening the conduit 76 to atmospheric pressure. Alternatively, a positive pressure can be applied by the pressure source 78 and the vacuum source 86 can consist of opening the conduit 84 to atmospheric pressure. The reservoirs 44, 46 and 48 are held at progressively lower pressures by pressure sources (not shown) in a range of pressures between that of the pressure source 78 and that of the vacuum source 86. Although it is preferable to maintain the chambers 12, 14, 16 and 18 at relatively constant pressures, other less desirable pressure arrangements are possible, such as having the chambers with varying liquid heights as shown in U.S. Pat. No. 3,793,587 to Thom et al. The providing of sheath flows for hydrodynamically focusing the particles as they pass through the sensing apertures, and the providing of sweep flow to prevent particles from recirculating back into the sensing zone of the third aperture 68, are well known techniques, as shown by U.S. Pat. No. 4,014,611 to Simpson et al. Although less desirable, as is well known, the sample suspension can be jetted through the first sensing aperture 60, thereby eliminating the need for a sheath flow from reservoir 44 for hydrodynamically focusing the particles. Likewise, although not desirable, the sweep flow after the third sensing aperture 68 is not essential. Other fluidic arrangements for accomplishing the objectives of the particle analyzer 10 embodying the invention will be obvious to those skilled in the art.

In operation, the sample suspension 72 of particles passes through the focusing tube 74, with the particles being hydrodynamically focused by a liquid sheath provided from the reservoir 44, as the sample and surrounding laminar sheath liquid pass through the first sensing aperture 60. The first sensing aperture 60 acts as a focusing tube for the second sensing aperture 64, with the liquid from the reservoir 46 forming a second liquid sheath for surrounding and hydrodynamically focusing the particles as they pass through the second sensing aperture 64. Likewise, the second sensing aperture 64 acts as a focusing tube for the third sensing aperture 68, with the liquid from the reservoir 48 forming a third liquid sheath for hydrodynamically focusing the particles as they pass through the third sensing aperture 68.

The electrodes 28, 30, 32, and 34 are electrically coupled to a plurality of electrical conductors 87, 88, 89 and 90, respectively. The conductor 90 is connected to a common ground 91. A current source 92 is electrically connected between the conductor 87 and the ground 91 so as to provide a D.C. electrical current through the sensing apertures 60, 64 and 68. The conductors 87, 88, and 89 are electrically coupled through a plurality of D.C. blocking capacitors $C_1$, $C_2$ and $C_3$, respectively, to a plurality of amplifiers 93, 94, and 95, respectively. A differential amplifier 96 is coupled to the outputs of the amplifier 93 and 94, so as to generate discrete particle pulses from the first sensing aperture 60. A differential amplifier 98 is coupled to the outputs of the amplifiers 94 and 95, so as to generate discrete particle pulses from the second sensing aperture 64. The output of the amplifier 95 is coupled to the detector 106 so as to generate discrete particle pulses from the third sensing zone 68. The outputs of the differential amplifiers 96 and 98 and the amplifier 95 are electrically coupled to a plurality of detectors 102, 104 and 106, respectively, for detecting the particle pulses. The detectors 102 and 104 detect particle pulses from the D.C. currents and the detector 106 detects particle pulses from the RF current. Although the electrodes are shown in the chambers, they can likewise be positioned in their respective liquid reservoirs. The current source and detectors are of well known conventional design.

In operation the current source produces an electrical field and sensing zone in each of the sensing apertures, causing each particle to modulate each electrical field, and hence the electrode currents, to generate three discrete analog particle pulses. The detectors detect the particle pulses and include electronic circuitry for measuring the height of individual particle pulses at some pulse threshold height level. In the embodiment of FIG. 1, the current source 92 provides a D.C. current, although, as previously explained, it is known that low frequency currents can also be used. Below the membrane voltage required to cause dielectric breakdown of cells, the pulse heights approximately correlate with the size or volume of the cells. Above the membrane voltage required to cause dielectric breakdown of cells, the pulse heights approximately correlate with the internal conductivity of the cells, as well as their size and breakdown potential. It will be obvious to those skilled in the art that there will be other ways to extract volume or internal conductance information from the discrete particle pulses, other than using the pulse height at its peak or some threshold pulse height. Hereinafter these extracted size and conductance signals will be referred to as "particle pulse signals".

The detectors 102, 104 and 106 are coupled by cables 108, 110, and 112, respectively, to a data processor 114. In a well known manner, the data processor includes analog to digital converters for digitizing the analog signals from the detectors and a computer for processing the digitized data. For an individual particle, the computer correlates the pulse height measurements of the three sensing apertures. Alternatively, known hardware delay circuitry can be used for correlating the particle pulse signals on a cell by cell basis. The digitized data for a given particle can be used by the computer to create the hereinafter described breakdown graph for the given particle. From this graph, desired data will be extracted and displayed to the user by output display means 116 or like output means.

The field strengths of the sensing apertures are set so as to measure the particle signals at three different field strengths ($E_i$): $E_1$ for the first sensing aperture 60; $E_2$ for the second sensing aperture 64; and $E_3$ for the third sensing aperture 68. Two of the field strengths, $E_2$ and $E_3$, are set, normally through trial and error, to be above the breakdown field strength, $E_c$, while the third field strength $E_1$ is set below the breakdown field strength $E_c$. Preferably, each successive field, relative to the particle's travel, is progressively stronger. However, since biological cells recover quickly after breakdown, with sufficient spacing between sensing apertures, it is possible, but not desirable, to have any order, random or otherwise, of the successive intensities. In the preferred embodiment, to have greater field intensities in each successive sensing aperture, the diameter of the sensing apertures are decreased. More specifically, in each sensing aperture, the field intensity $E_i$ can be expressed in the following equation:

$$E_i = V_i/l_i = (I_i \rho)/A_i$$

where $V_i$ is the voltage across the sensing aperture, $l_i$ is effective electrical length of the aperture, $I_i$ is the current through the aperture, $\rho$ is the resistivity of the sensing aperture, and $A_i$ is the cross-sectional area of the sensing aperture. Thus, for example, if $E_1=0.8E_c$, $E_2=1.2E_c$, and $E_3=1.6E_c$, the corresponding cross-sectional areas $A_i$ of the sensing apertures would have the ratio of 1:0.666:0.5, respectively. Alternatively, the voltages $V_i$ across the sensing apertures could be successively increased to give the desired increasing field intensities. In order to do this, either current sources would have to be attached to electrodes 88 and 89 in FIG. 1, or a potential divider network external to the orifices set up, or other means can be used, as will be explained in more detail hereinafter.

Figure 2:
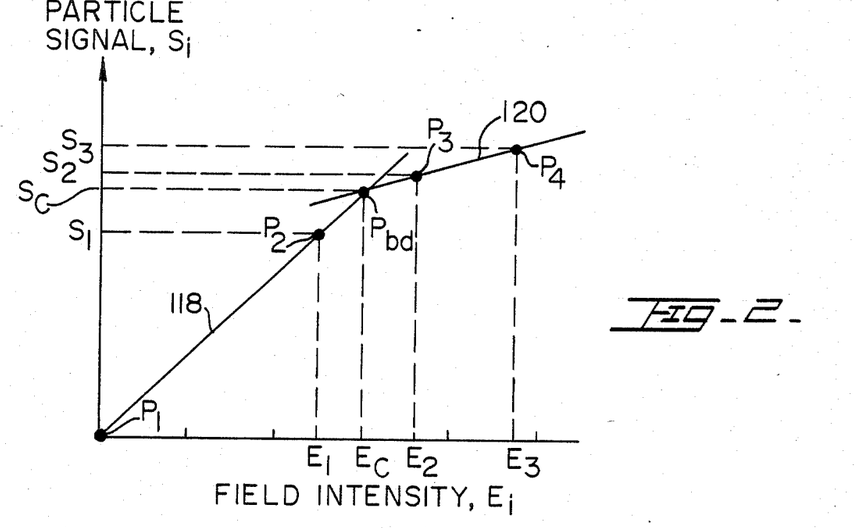
FIG. 2 is a graph of data obtained for a given cell which is used to calculate the apparent electrical breakdown parameter for the cell.

FIG. 2 graphically illustrates in a chart one possible set of calculations performed by the computer of the data processor 114 for a given particle at the three above-described field intensities. The three particle signals $S_i$, one for each of the three sensing zones, are plotted against the corresponding field intensities $E_i$. This data from the sensing apertures defines three points $P_2$, $P_3$, and $P_4$. It is well known that the particle signal $S_i$, as plotted against intensity, increases substantially linearly from a Point $P_1$ (0,0 coordinates) of the chart to the breakdown field intensity $E_c$ and increases substantially linearly after the breakdown field intensity, but at a lesser slope. Since we have two points ($P_1$, $P_2$) on the first leg of the plot, the computer can define a straight line 118 between $P_1$ and $P_2$ and can extrapolate the same forward and upward therefrom. Since we have two points ($P_3$, $P_4$) on the second leg of the curve of the plot, the computer can define a straight line 120 between the points $P_3$ and $P_4$ and can extrapolate the same backward. Where the two lines intersect and cross over, a point $P_{bd}$ is defined, which has an abscissa value approximating the apparent breakdown field intensity $E_c$. From the data used in this graph, the computer can provide, for example, to the user, by way of the output display 116, three measurements for each cell: cell size (volume), breakdown field voltage and the internal conductivity. The cell size can be calculated from the slope of the line 118. The intersection of the two lines 118 and 120 gives the breakdown field intensity $E_c$ from which the breakdown voltage of the particle's membrane can be calculated, given the size, shape and orientation of the particle in the imposed fields. As taught in U.S. Pat. No. 4,298,836 to Groves et al., the opacity can be calculated from the ratio of the slope of the line 120 to the slope of the line 118. From this, knowing the particle volume, shape and orientation and the external fluid conductivity, the particle internal conductivity can be obtained.

From the data contained in the chart of FIG. 2, the mathematics for calculating these three measurements are well known to those skilled in the art. Additionally, the computer, using a plotter, can also print out the graph of FIG. 2. As will be obvious to those skilled in the art, different information can be calculated and accessed in different forms.

In the preferred computer implementation, it is desirable to mathematically calculate the breakdown field intensity, instead of actually extrapolating the heretofore described two lines 118 and 120 of a graph. The field intensity can be calculated numerous ways, one way being with the following equation:

$$E_c = (S_3 \cdot E_1/S_1 - E_3 \cdot O_p)/(1 - O_p)$$

where $O_p$ (opacity) = (Slope of line 120)/(Slope of line 118)

Figure 3:
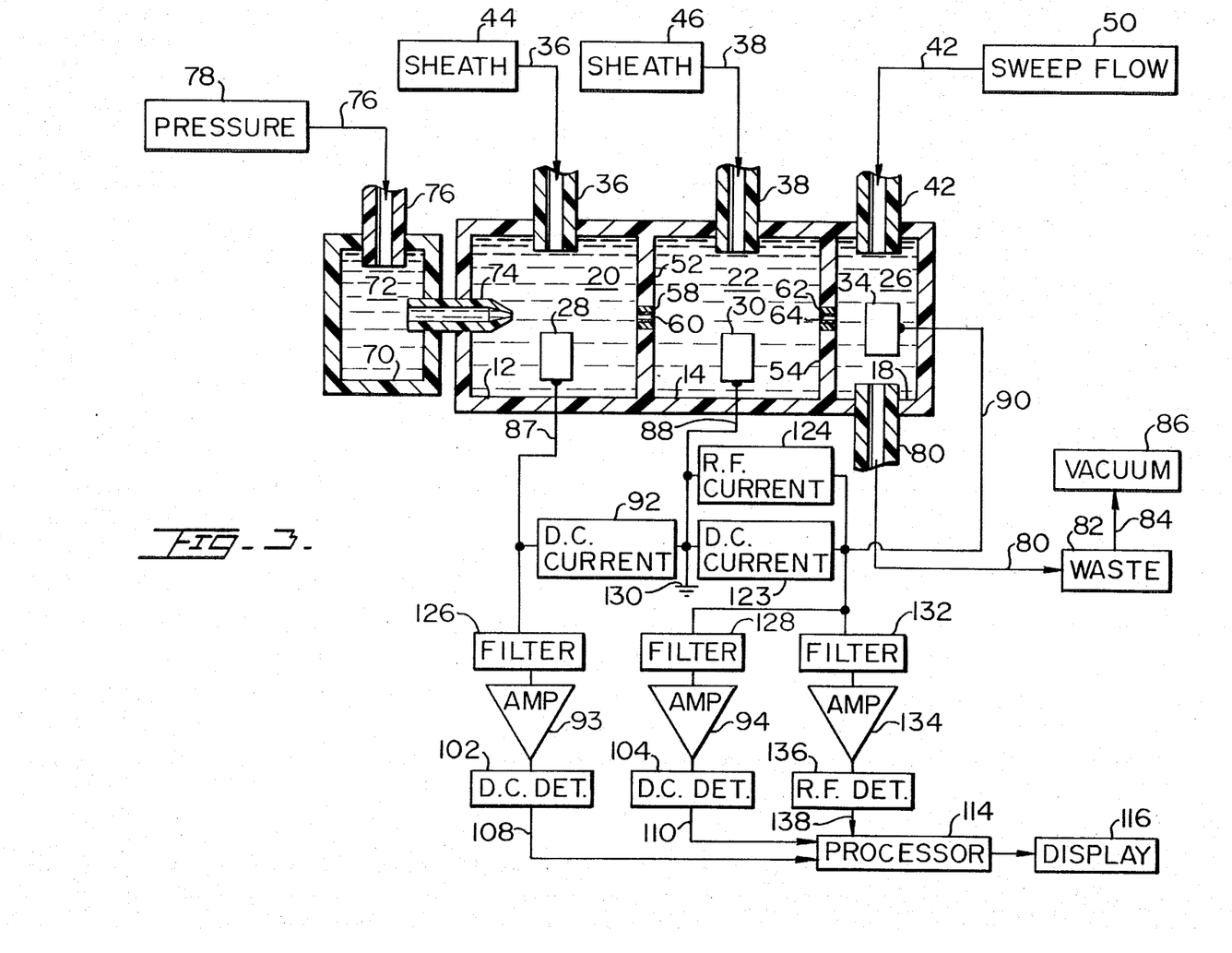
FIG. 3 is a diagrammatical view of an alternative embodiment of the particle analyzing apparatus.

FIG. 3 shows an alternative embodiment of the particle analyzing apparatus 10. The embodiment of FIG. 3 is the same as FIG. 1, except for the hereinafter described changes. First, the elements in dashed box 122, in FIG. 1, are not included in the embodiment of FIG. 3. Hence, there are only three chambers, two sensing apertures, two sheath reservoirs, and three electrodes. This reduction in structure results from a change in the current source and detection circuitry so as to pass simultaneously a D.C. (or low frequency) and a high frequency, such as radio frequency (R.F.), through the sensing aperture 64. Specifically, the D.C. current source 92 is coupled to the electrodes 28 and 30 via the conductors 87 and 88, respectively. A second D.C. current source 123 is coupled to the electrodes 30 and 34 by way of the conductors 88 and 90, respectively. Additionally, an R.F. current source 124 is coupled to the electrodes 30 and 34 via the conductors 88 and 90, respectively. As shown in FIG. 3, a pair of low bandpass filters 126 and 128 preferably replace the capacitor couplings of the amplifiers 93 and 94 shown in FIG. 1. The electrical conductor 88 is electrically coupled to a common electrical ground 130. The electrical conductor 90 is coupled through a high band-pass filter 132 to an amplifier 134, which in turn is electrically coupled to an R.F. detector 136. The two low band-pass filters 126 and 128 pass, for example, frequencies in the band from mid-audio frequencies to about 80 kilohertz, since this is the band in which the pulse energy due to particle pulses is normally found. The high band-pass filter 132, for example, can be centered on the R.F. carrier frequency and can, for example, encompass 160 kilohertz. These filters have the dual function of preventing the steady-state voltage across the aperture, which is either DC or radio frequency, from saturating the corresponding amplifier and at the same time separate the low frequency signals from the high frequency signals. Consequently, from the sensing aperture 68, an R.F. or like high frequency signal and a D.C. or low frequency signal are simultaneously obtained. As with the two D.C. particle signals, the R.F. particle signal is fed to the data processor 114 via an electrical cable 138. The electronic circuitry for energizing the apertures and for detecting and processing the particle pulse are well known, as shown in U.S. Pat. Nos. 3,502,973 and 3,502,974.

The operation of the embodiment of FIG. 3 and the acquisition of data therefrom is the same as the embodiment of FIG. 1, except only two sensing apertures are needed, with the R.F. particle pulse signal substituting for one of the D.C. particle pulse signals obtained after breakdown in the super-critical field range. More specifically, referring to FIG. 2, the R.F. particle pulse signal can be used to define the slope of the line 120, with the DC signal $P_3$ or $P_4$ defining a point through which this line must pass. The reason for this is the R.F. current, in the same manner as a high D.C. current, shunts the cell's membrane, so that the resulting change in signal with applied field is substantially related to the internal conductivity, size and shape of the cell.

Although the operation of the particle analyzing apparatus 10 has primarily been described as operating on biological cells, those skilled in the art will realize that these techniques are equally applicable for biological cells that have been modified or for other membrane-sheathed particles having internal constituents which are electrically relatively conductive with respect to the membrane, with the membrane having a substantial capacitance and a relatively higher resistance with respect to the internal constituents.

Figure 4:
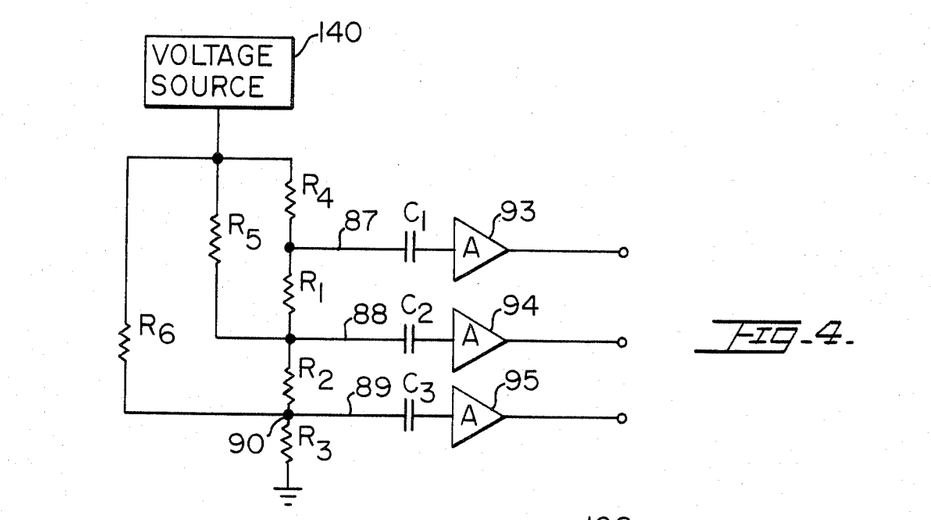
FIG. 4 is a schematic view of a modification to the electrical circuit of the embodiment of FIG. 1.

As previously described, the different field strengths in the sensing apertures of FIGS. 1 and 3 were achieved by having apertures of different cross-sectional areas. However, as shown in the electrical schematic of FIG. 4, the different field strengths can also be obtained by a voltage divider network. Although equally utilizable for either embodiments of FIGS. 1 or 3, the divider network is shown implemented in the three sensing aperture arrangement of FIG. 1. A constant voltage is provided by a voltage source 140 to power electrodes (not shown) in each of the chambers 12, 14, 16, and 18. The electrical resistances of the sensing apertures 60, 64 and 68 are shown as $R_1$, $R_2$ and $R_3$, respectively. The voltage source 140 is coupled to an electrode in chamber 12 through a resistor $R_4$, to an electrode in chamber 14 through a resistor $R_5$, to an electrode in chamber 16 through a resistor $R_6$. Preferably, but not necessarily, sensing electrodes, separate from the power electrodes, are positioned in chambers 12, 14 and 16 to detect particle pulses and are coupled to the amplifiers 93, 94 and 95 by way of the conductors 87, 88 and 89, respectively. The remainder of the circuitry remains the same as in FIG. 1 and is not shown. The use of separate power and sensing electrodes is well known, as shown in U.S. Pat. No. 4,019,134 to Hogg.

Figure 5:
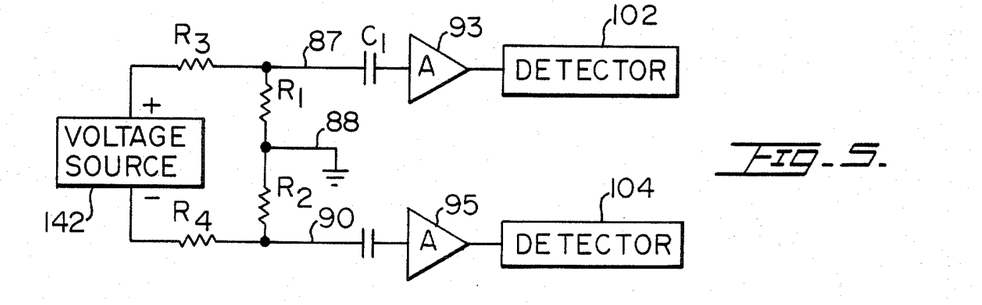
FIG. 5 is a schematic view of the broadest inventive concept of the particle analyzing apparatus.

FIG. 3 can be used to show the minimal structure and signals required for the broadest scope of the invention. In this broad conceptualization, only two signals are required, the particle pulses from the detectors 102 and 104. With this simplified design, for a given particle, one particle pulse is obtained with an electrical field below breakdown strength and one particle pulse is obtained with an electrical field above breakdown strength. Although the breakdown field strength $E_c$ cannot be obtained from just these two signals, the two particle pulses, when correlated on a cell by cell basis, are useful for detecting cells in different pathological states, e.g., with differing internal conductivities or deformabilities. FIG. 5, in combination with FIG. 3, illustrates the simplified structure of this broad concept and differs from that simplified structure described with respect to FIG. 3 only in that a voltage divider network with the same size sensing apertures is used, instead of the constant current source and different size sensing apertures shown in FIG. 3. The sensing apertures 60 and 64 are shown by their electrical resistances $R_1$ and $R_2$, respectively. A voltage source 142 is coupled to a power electrode (not shown) in the chamber 12 by way of an electrical resistor $R_3$ and to a power electrode in the chamber 18 by way of an electrical resistance $R_4$, with the chamber 14 being grounded by way of the conductor 88. The amplifiers 93 and 95 remain capacitively coupled to the electrodes 28 and 34, respectively, but are now directly coupled to the detectors 102 and 104.

Scientific research has indicated that the actual breakdown voltage $V_c$ across the membrane remains relatively constant. Cell shape factor variations will be reflected in both the apparent cell size and the breakdown field, $E_c$. Hence, the determination of the breakdown field $E_c$ or membrane voltage $V_c$, according to the teachings of the present invention, can be particularly useful. For instance, it has been found that the breakdown field $E_c$ can be dependent upon cell age. The older, denser cells are more resistant to the electrical field, which results from their inability to deform as much as younger cells.

The following equations will be useful in showing how the breakdown field $E_c$ can be useful:

$$S = f \cdot Vol \qquad (1)$$

and $$V_c = f \cdot a \cdot E_c \qquad (2)$$

and where "f" is the shape factor of the particle in the orifice, "Vol" is true volume, "S" is the apparent particle size, "a" is the long semi-axis of the particle, and "$V_c$" is the critical breakdown voltage across the membrane of the particle.

By rearranging Equations (1) and (2), the following is obtained:

$$Vol = \frac{S}{f} \qquad (3)$$

$$a = \frac{V_c}{f \cdot E_c} \qquad (4)$$

Additionally, by definition of a prolate ellipsoid:

$$RT = \left(\frac{4 a^3}{3 Vol}\right)^{\frac{1}{2}} \qquad (5)$$

and $$f = \frac{1}{\left(\dfrac{RT^2}{RT^2 - 1} - \dfrac{RT \cdot \cosh^{-1}(RT)}{(RT^2 - 1)^{3/2}}\right)} \qquad (6)$$

and where "RT" is the ratio of the long to short axis of an ellipsoid.

If the above equations are written only in terms of functional relationships, such that a=F(b) reads: "a" is a function of "b", then (5) and (6) can be rewritten as:

$$RT = F(a, Vol) \qquad (7)$$

and $$f = F(RT) \qquad (8)$$

Combining (7) and (8), the following can be written:

$$f = F(a, Vol) \qquad (9)$$

i.e., "f" is purely a function of "a" and "Vol".

Substituting for "f" in (3) and (4) using (9), the following is obtained:

$$Vol = \frac{S}{F(a, Vol)} \qquad (10)$$

and $$a = \frac{V_c}{F(a, Vol) E_c} \qquad (11)$$

The above equations (10) and (11) are a simultaneous pair and, provided S and $E_c$ are measured and $V_c$ is a given constant, there are two equations with only two unknowns, "a" and "Vol".

Hence, one may obtain unique values for the particle volume and the associated major axis. Returning these values to equation (5) yields the shape of the particle, RT. For erythrocytes, this is a very useful measure of their deformed state as they pass through an aperture or, alternatively, of their ability to deform.

For erythrocytes of differing ages, the data below was obtained:

| Erythrocyte age | S (fl) | $E_c$ (V/cm) | $V_c$ | f | RT | Vol |
|---|---|---|---|---|---|---|
| Old | 79 | 2900 | 1.05 | 1.24 | 1.8 | 64 |
| Middle | 83 | 1950 | 1.05 | 1.11 | 3.2 | 75 |
| Young | 83 | 1790 | 1.05 | 1.09 | 3.75 | 76 |

It will be noted that while the measured size did not vary appreciably, the breakdown field varied by 65% in response to the older cells' lack of ability to deform, which is a feature well documented in the scientific literature.

If the analysis is taken a step further, the internal conductivity of the particle, as taught in U.S. Pat. No. 4,298,836 to Groves et al., can be determined from the measured opacity and calculated shape factor:

$$\sigma_i = \sigma_e \left( \frac{1 - O_p}{1 + (f - 1)O_p} \right)$$

where $O_p$=Opacity, $\sigma_{i,e}$=Conductivities, internal and external respectively, and f=shape factor.

Reference to direct current or voltage sources 92, 123, 140 and 142 are not intended to exclude low frequency sources. These sources will be described in the claims as "low frequency" sources, with a direct current being considered to be of zero frequency in this application. The sources must have such a low frequency that the reactive effects on the circuit are of no consequence. Particle pulse signals produced by these sources, when the sensing apertures are excited by a direct or low frequency current, are quite proportional to the size or volume of the particle. Likewise, the R.F. current source 124 encompasses frequencies high with respect to the low frequency sources 92, 123, 140 and 142 and will be defined as a "high frequency" source or current in the claims. The current source 124 can be any high frequency whereat the capacitance of the membrane shunts the membrane resistance, which for biological cells in the micron size range is in the radio frequencies.

Although particular embodiments of the invention have been shown and described herein, there is no intention thereby to limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. A particle analyzing apparatus for studying a stream of membrane-sheathed particles in liquid suspension, wherein the particles individually undergo electrical breakdown in an electrical field having at least a minimum electrical breakdown field intensity, said particle analyzing apparatus comprising:

at least two sensing aperture means, including a first sensing aperture means and a second sensing aperture means;

means for moving the liquid suspension of the particles sequentially through all of said sensing aperture means;

first field generating means, for providing a low frequency first electrical field in said first sensing aperture means, having an electrical field intensity less than said minimum electrical breakdown field intensity;

first detecting means responsive to electrical impedance variation for generating a first particle pulse signal with the passage of a given particle through said first sensing aperture means;

second field generating means, for providing a low frequency second electrical field in said second sensing aperture means, having an electrical field intensity which is at least as great as said electrical breakdown field minimum intensity;

second detecting means responsive to electrical impedance variations for generating a second particle pulse signal with the passage of the given particle through said second sensing aperture means; and means for correlating said first and second particle pulse signals for the given particle.

2. The particle analyzing apparatus according to claim 1, further comprising, po0 third field generating means, for providing a third electrical field in a sensing aperture means, having a frequency or intensity for causing at least some of an electrical current to pass through the particles; and third detecting means responsive to electrical impedance variations for generating a third particle pulse signal with the passage of the given particle through said sensing aperture means having said third electrical field, and wherein said means for correlating includes means for correlating said third particle signal with said first and second particle signals for the given particle.

3. The particle analyzing apparatus according to claim 2, further comprising, means for determining an apparent electrical breakdown parameter for the given particle from said first, second and third particle signals for that given particle.

4. The particle analyzing apparatus according to claim 3, wherein said apparent electrical breakdown parameter consists of an electrical field intensity.

5. The particle analyzing apparatus according to claim 4, further comprising, means for determining shape information about the given particle from said apparent electrical breakdown parameter for the given particle.

6. The particle analyzing apparatus according to any one of claims 2 through 5, wherein said third field generating means generates said third electrical field in a third sensing aperture means with a low frequency.

7. The particle analyzing apparatus according to any one of claims 2 through 5, wherein said third field generating means generates said third electrical field in one of said first and second sensing aperture means with a high frequency.

* * * * *

UNITED STATES PATENT AND TRADEMARK OFFICE
CERTIFICATE OF CORRECTION

PATENT NO. : 4,525,666
DATED : July 25, 1985
INVENTOR(S) : Michael Robert Groves It is certified that error appears in the above—identified patent and that said Letters Patent is hereby corrected as shown below:

Column 12, line 28, after "comprising," delete "po0".

Signed and Sealed this

Seventeenth Day of September 1985

[SEAL]

Attest:

Attesting Officer

DONALD J. QUIGG

Commissioner of Patents and
Trademarks—Designate